US008452379B2

(12) United States Patent
DeFreitas et al.

(10) Patent No.: US 8,452,379 B2
(45) Date of Patent: *May 28, 2013

(54) X-RAY MAMMOGRAPHY WITH TOMOSYNTHESIS

(75) Inventors: Kenneth F. DeFreitas, Patterson, NY (US); Baorui Ren, Andover, MA (US); Chris Ruth, Danvers, MA (US); Ian Shaw, Yorktown Heights, NY (US); Andrew P. Smith, Lexington, MA (US); Jay A. Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 12/879,807

(22) Filed: Sep. 10, 2010

(65) Prior Publication Data

US 2011/0069808 A1    Mar. 24, 2011

Related U.S. Application Data

(62) Division of application No. 10/723,486, filed on Nov. 26, 2003, now Pat. No. 7,831,296.

(51) Int. Cl.
*A61B 5/05* (2006.01)

(52) U.S. Cl.
USPC ............ 600/427; 378/37; 600/425; 600/426; 600/429

(58) Field of Classification Search
USPC .................... 378/37; 600/407, 425, 426, 427, 600/429
See application file for complete search history.

(56) References Cited

U.S. PATENT DOCUMENTS

| 5,553,111 | A  | * | 9/1996  | Moore et al. ............. 378/37 |
| 5,941,832 | A  | * | 8/1999  | Tumey et al. ............. 600/549 |
| 6,292,530 | B1 |   | 9/2001  | Yavus et al. |
| 6,574,304 | B1 |   | 6/2003  | Hsieh et al. |
| 6,647,092 | B2 |   | 11/2003 | Eberhard et al. |
| 6,751,285 | B2 | * | 6/2004  | Eberhard et al. ......... 378/37 |
| 6,882,700 | B2 |   | 4/2005  | Wang et al. |
| 6,885,724 | B2 |   | 4/2005  | Li et al. |
| 6,909,792 | B1 | * | 6/2005  | Carrott et al. ............. 382/128 |
| 6,940,943 | B2 |   | 9/2005  | Claus et al. |
| 6,999,554 | B2 |   | 2/2006  | Mertelmeier |
| 7,110,490 | B2 |   | 9/2006  | Eberhard et al. |
| 2003/0026386 | A1 | | 2/2003  | Tang et al. |
| 2003/0169847 | A1 | | 9/2003  | Karellas et al. |
| 2003/0212327 | A1 | | 11/2003 | Wang et al. |

* cited by examiner

*Primary Examiner* — Long V. Le
*Assistant Examiner* — Ellsworth Weatherby
(74) *Attorney, Agent, or Firm* — Cooper and Dunham LLP

(57) ABSTRACT

A method and system for producing tomosynthetic images of a patient's breast. An x-ray source that delivers x-rays through a breast immobilized and compressed between a compression paddle and a breast platform and form an image at a digital x-ray receptor panel. Multiple x-ray images are taken as the x-ray source and the receptor move relative to the immobilized breast. In one preferred embodiment, the x-ray source travels from −15° to +15°. The source can travel in an arc around the breast while the receptor travels linearly while remaining parallel and at the same distance from the breast platform. The sets of x-ray image data taken at different angles are combined to form tomosynthetic images that can be viewed in different formats, alone or as an adjunct to conventional mammograms.

14 Claims, 5 Drawing Sheets

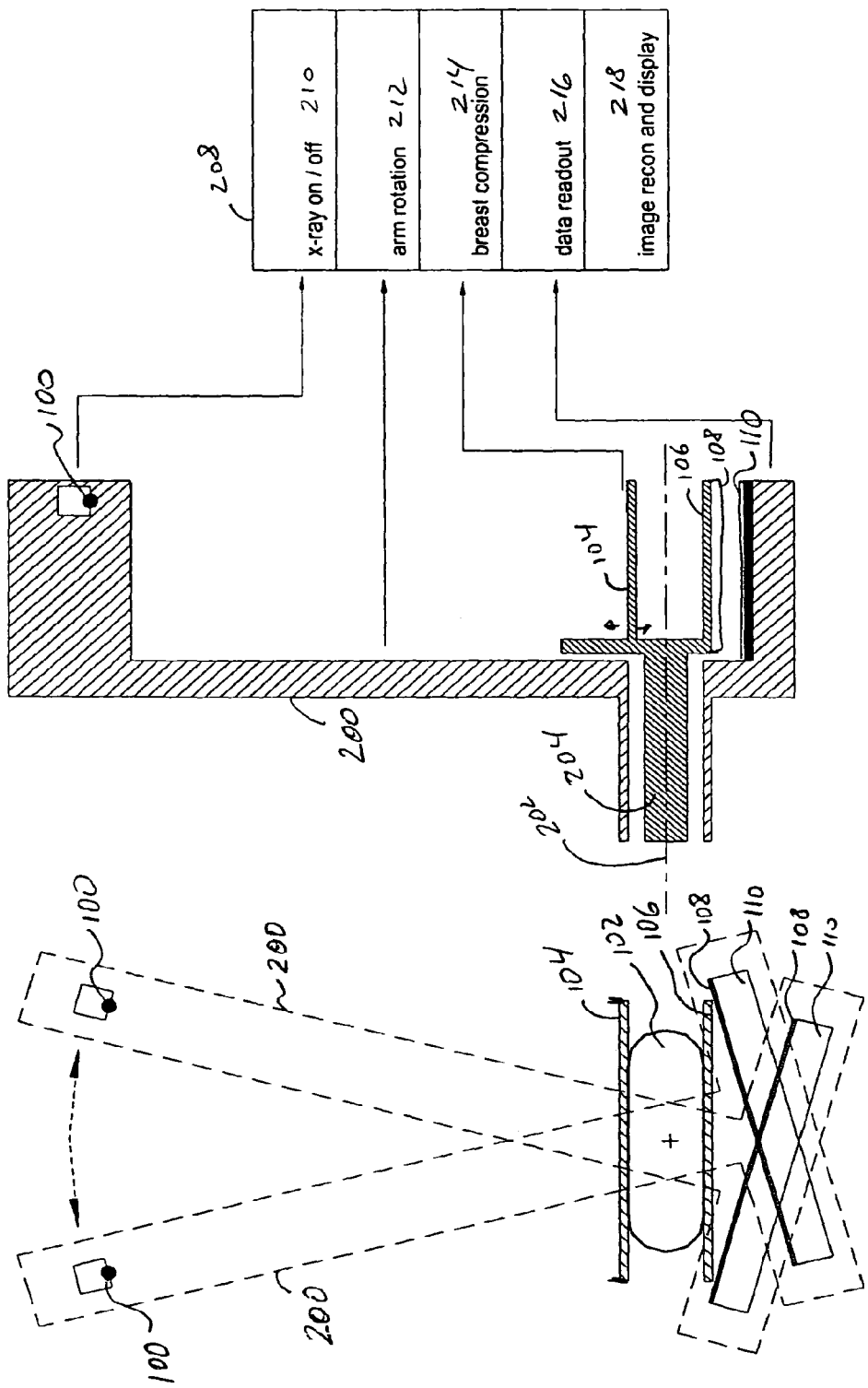

X-RAY MAMMOGRAPHY WITH TOMOSYNTHESIS

CROSS-REFERENCE TO RELATED APPLICATIONS

This application is a divisional of U.S. application Ser. No. 10/723,486, filed Nov. 26, 2003, Now U.S. Pat. No. 7,831,296, issued on Nov. 9, 2010.

FIELD

This patent specification is in the field of x-ray imaging of the breast and, more specifically, obtaining and processing x-ray data for tomosynthesis.

BACKGROUND

Breast cancer remains an important threat to women's health. X-ray mammography currently is the most widely used breast imaging tool for early detection, and is the modality approved by the Food and Drug Administration to screen for breast cancer in women who do not show symptoms of breast disease. A typical mammography system takes a projection image of the compressed breast, using a collimated x-ray source at one side and a film/screen unit at the other side of the breast. In the United States, typically two views are taken of each breast, one from above (cranial-caudal, or CC) and one from the side (mediolateral-oblique, or MLO). The x-ray source is an x-ray tube typically operating at 25-40 kVp, using a molybdenum or rhodium rotating anode with a focal spot of about 0.3-0.4 mm and, in some cases, 0.1 mm or less. An anti-scatter grid between the breast and the film/screen unit reduces the effects of x-ray scatter. The screen converts x-ray energy to visible light to which the film is exposed to record the image. In each view, the breast is compressed to reduce patient motion and also for reasons such as reducing scatter, separating overlapping structures in the breast, making the thickness of the imaged breast more uniform, and providing more uniform x-ray exposure. Currently, flat panel array receptors are replacing the film/screen units in mammography systems. The Selenia™ digital mammography system with such a flat panel x-ray receptor is offered by Lorad, a subsidiary of the assignee Hologic, Inc. of Bedford, Mass. Digital mammography has significant advantages and in time may fully supplant film/screen systems. Additional information regarding digital mammography systems and processes offered by the common assignee can be found at <www.hologic.com>.

Mammograms, whether from film/screen units or from digital systems, are particularly difficult to read, and the rate of false negatives and false positives is significant. Many advances have been made in recent years in image acquisition and in image processing, but a need still remains to reduce the rates of false negatives and positives, at least in screening mammography. Additional information can be gained through modalities such as CT and MRI, but examination and interpretation time and cost and other factors have limited their use in screening for breast cancer. Ultrasound breast examination has been proposed as an adjunct to x-ray examination, with synthesized ultrasound images of thick slices of the breast as they would appear in the same projection view as an x-ray view displayed together with the x-ray view, and a unit taking both x-ray and ultrasound images has been proposed. See, e.g., Patent Application Publication No. U.S. 2003/0007598 A1 and U.S. Pat. No. 5,983,123. Digital tomosynthesis has been proposed for x-ray breast imaging, and a laboratory unit is believed to have been installed at the Massachusetts General Hospital (more than a year before the filing date hereof), as reported in Wu, Tao, 2002, *Three-Dimensional Mammography Reconstruction Using Low Dose Projection Images*, PhD thesis, Brandeis University, incorporated here by reference. See, also, Patent Application Publication No. 2001/0038681 A1 and PCT application International Publication No. WO 03/020114 A2 published Mar. 13, 2003, both incorporated herein by reference. Digital tomosynthesis in more general contexts also has been proposed. See, e.g., U.S. Pat. Nos. 6,289,235 and 5,051,904, commonly assigned U.S. Pat. No. 4,496,557, and Digital Clinical Reports, Tomosynthesis. GE Brochure 98-5493, 11/98, all incorporated herein by reference. Reference markers can be used in x-ray imaging for purposes such as checking the rotation angle and unwanted shift of center of rotation of an x-ray source and receptor, and fiducial phantoms can be used in 3D angiography to calibrate for irregular scan geometries. See, e.g., U.S. Pat. Nos. 5,051,904, 5,359,637, and 6,289,235, N. Navab, et al., *Dynamic geometrical calibration for 3D cerebral angiography*, SPIE Vol. 2708, pp. 361-370, and said PCT published application WO 03/020114 A2, all incorporated by reference here.

It is believed that no breast tomosynthesis systems are commercially available currently for clinical use in breast imaging, and that improvements in x-ray imaging and tomosynthesis are a desired goal. Accordingly, it is believed that a need remains for improved and practical tomosynthesis mammography.

SUMMARY

In a typical x-ray imaging according to preferred embodiments disclosed in this patent specification, a patient's breast is immobilized, at the same or lower compression than in conventional mammography, between a breast platform and a compression paddle. The platform and paddle, and the breast between them, in turn are between an x-ray source and a digital imaging receptor. Unlike conventional x-ray mammography, in which typically a breast is imaged from only one angle at a given compression, here the immobilized breast is imaged with x-rays from the source that pass through the breast and impinge on the receptor, from a greater number of different positions of the source and receptor relative to the breast while maintaining the breast immobilized, to derive image data for the respective positions. To do this, the x-ray source moves around the immobilized breast, typically but not necessarily in an arc, and the receptor also moves relative to the breast, but in a motion that allows it to remain substantially parallel to the same plane. The x-ray data taken at each of a number of positions of the receptor relative to the breast is processed to form images where each of a number of the images is formed from image data acquired from two or more of the different positions, e.g., to form tomosynthetic images. The x-ray dose to the breast can be different for the different imaging positions. One or more of the imaging positions can use an x-ray dose comparable to that used for conventional mammography. These positions may be the same or similar to the source/receptor positions for the typical views used in conventional mammography, e.g., the CC view and the MLO view. Fiducial markers can be used to help assess the positions of the x-ray source and x-ray receptor relative to each other and/or the breast being imaged, and for other calibration purposes. The fiducial markers can be integrated with the compression paddle and/or the breast platform, or can be positioned otherwise to serve the intended purpose. The immobilized breast can be imaged at angular positions extending over a selected range around the immobilized breast, for example ±15°, although other ranges can be used in other examples. The motion can be continuous over some or all of the imaging positions, or can be intermittent such that the x-ray source and/or the x-ray receptor stop for taking and image and then move to the next position for the next image.

An antiscatter grid can be used, positioned between the breast platform and the x-ray receptor while x-ray image data are taken. One example is the grid available from Lorad under the tradename HTC® grid. Alternatively, the image data at some or all of the imaging positions can be taken without an antiscatter grid that is external to the x-ray receptor. Rather than using the currently conventional materials for the x-ray emitting target in an x-ray tube serving as the x-ray source, in one of the preferred embodiments the target is made essentially of Tungsten, to provide x-rays at energies that are believed more suitable for breast x-ray tomosynthesis. Geometries other than an x-ray source that rotates around the immobilized breast and an x-ray receptor that moves relative to the breast and the source but remains in substantially parallel to the same plane, can be used.

Image data taken at the different imaging positions can be processed to generate tomosynthetic images of selected slices of the breast. The images can be of thin slices, essentially planar sections through the breast, as in CT slices. Alternatively, they can be of thick slices of the breast, e.g., slices that are about 0.5 cm to about 1.0 cm thick, and simulate projection images of slices of that thickness, projected on one or more selected image planes. In one example, the image plane or planes of the thick slice images are the same as those of the typical conventional mammograms, and can be displayed for viewing in appropriate groupings. For example, projection-like tomosynthetic images of thick slices on a plane parallel to that of a conventional CC image can be displayed together with a conventional CC image of a breast, on the same screen or adjacent screens or other displays. Similarly, projection-like tomosynthetic images of thick slices on plane parallel to that of an MLO image can be displayed on the same display or on adjacent displays with a conventional MLO mammogram of the same breast. In the alternative, the image planes of the tomosynthetic images can be at one or more selected angles to the image planes of the typical images used in screening x-ray mammography.

Tomosynthetic images can be formed using a form of filtered backprojection modified by using a filter function that is significantly different from a conventional ramp filter used in CT technology backprojection. The novel filter function is believed to be uniquely suited to breast tomosynthesis. In particular, in the frequency domain the novel filter function at low spatial frequencies is much steeper than a CT technology ramp function, it is close to an all-pass filter at intermediate frequencies, and at higher frequencies it falls off to suppress fine detail noise.

BRIEF DESCRIPTION OF THE DRAWING

FIGS. 7 and 8 are similar to FIGS. 1 and 2, respectively, but illustrate another preferred embodiment.

DETAILED DESCRIPTION OF PREFERRED EMBODIMENTS

Figure 1:
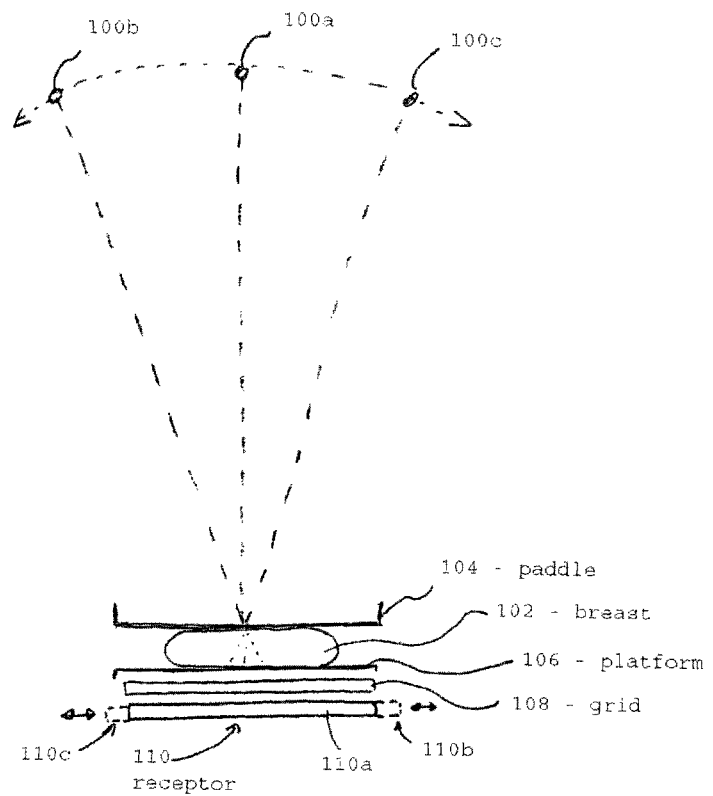
FIG. 1 illustrates schematically a front view of an x-ray source, a breast immobilized between a compression paddle and a breast platform, an antiscatter grid and an image receptor, where the x-ray source and the x-ray receptor move relative to the breast for imaging the breast at different angles according to a preferred embodiment.

FIG. 1 schematically illustrates in front view an x-ray source 100 in three different positions 100a, 100b and 100c, between which source 100 moves in an arc centered at the top center of a patient's breast 102 immobilized between a compression paddle 104 and a breast platform 106. An antiscatter grid 108 is immediately below breast platform 106, and an x-ray receptor 110 is below grid 108, and is shown in three different positions, 110a, 110b, and 110c, corresponding to the illustrated positions of source 100. Receptor 110 moves relative to immobilized breast 102 along a path substantially parallel to breast platform 106 and maintains substantially the same distance from platform 106, as indicated by the arrows in FIG. 1. In operation, source 100 moves from one of its illustrated position to another, and so does receptor 110. At each position of source 100 and receptor 110, source 100 is energized to emit a collimated x-ray beam, of which only the center ray is illustrated. The beam irradiates breast 102 and some of the radiation that has passed through the breast also passes through grid 108 and is received by receptor 110. As in known in the art, receptor 110 and associated electronics generate image data in digital form for each pixel of a rectangular grid of pixels at each of the illustrated angular position of source 100 and translation positions of receptor 110 relative to immobilized breast 102. While only three positions are illustrated in FIG. 1, in practice image data is taken at each of a much greater number of positions, for example, at every 1° of an arc of ±15° of source 100 around immobilized breast 102. The taking of image data can be while source 100 and receptor 110 are stopped at their respective positions, after moving from one position to the next. In a different preferred embodiment, the motion of one or both of source 100 and receptor 110 can be continuous, with a respective set of image data being accumulated over a small increment of continuous motion, say a 0.1° to 0.5° arc of motion of source 100. These parameters are only an example. Different preferred embodiments can use different ranges of motion of source 100 and receptor 110, and can use a motion of source 100 that is arcuate and centered at a different point, such as in immobilized breast 102 or at breast platform 106 or at grid 108 or at receptor 110, or a motion that is not arcuate but is translational or is a combination of different types of motions, such as partly translational and partly rotational. In the most preferred embodiment, the source 100 motion is arcuate and the receptor 110 motion is translational. As described further below, in practice source 100 can be integrated in a C-arm that is the same or similar to the C-arm used in the commercially available Selenia® or MIV mammography systems available from Lorad, and receptor 110 can be the same receptor as used in such commercially available systems but mounted differently so that it translates in a plane substantially parallel to breast platform 106 while maintaining a substantially constant distance from platform 106 rather that rotating as a unit with source 100, as in Lorad commercially available systems.

Figure 2:
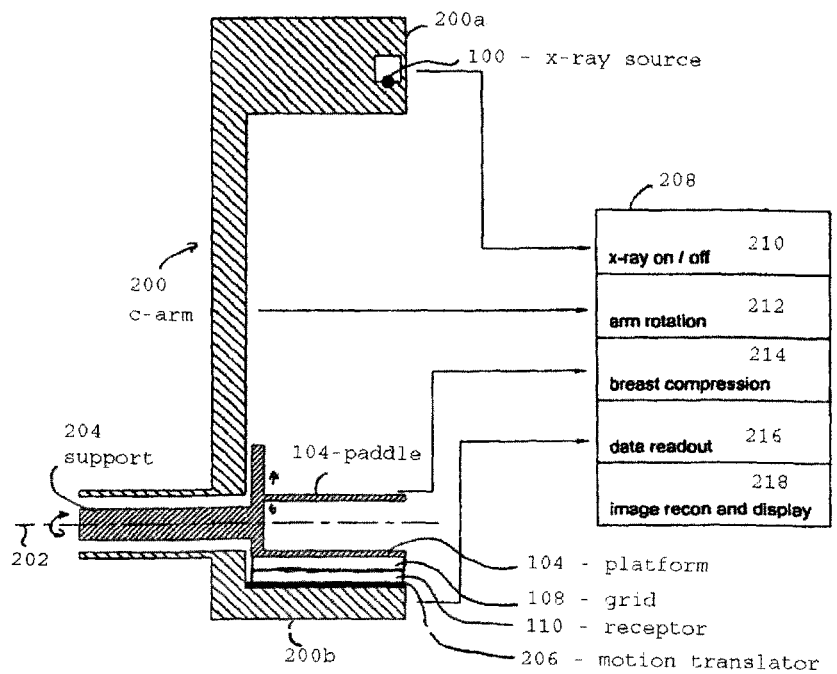
FIG. 2 illustrates a side view of the system illustrated in FIG. 1 and additional components of a system according to a preferred embodiment.

FIG. 2 schematically illustrates a side view of a mammography system using the arrangement of FIG. 1. In FIG. 2, x-ray source 100 is at one end 200a of a C-arm 200 that is supported for selective rotation about an axis 202, independently of a support 204 for compression paddle 104 and breast platform 106. Support 204 also selectively rotates about the same axis 202. The other end 200b of C-arm 200 interacts with x-ray receptor 110 through a motion translator schematically illustrated at 206 that translates the rotational motion of the end 200b about axis 202 to a substantially translational motion of receptor 110 that substantially maintains the distance of receptor 110 from breast platform 106 while x-ray data is being taken. FIG. 2 is not to scale, and receptor 110 can be spaced further from member 200b than illustrated, to allow more space for motion translator 206, and also to allow for receptor 110 to be moved selectively further from or closer to breast platform 104 and thus allow for x-ray image magnification. In operation, C-arm 200 and support 204 are rotated to desired angular positions, either manually or by motor drives, patient breast 102 is positioned on platform 106 and is immobilized by bringing paddle 104 toward platform 106 and compressing breast 102, with typically the same or less force than for a typical conventional mammogram, such as between one to one-third the conventional force. With breast 102 immobilized, and with C-arm at a selected angle relative to a normal to platform 106 and receptor 110, such as +15°, imaging starts, and a projection image is taken for each of a number of selected angular positions of source 100 while C-arm 200 rotates, continuously or intermittently, through a selected angle, such as an angle of 30°, is from +15° to −15°. Of course, the motion can be in the opposite direction, from −15° to +15°, or can be over a different angular interval, such as over less than a total of 30°, e.g. 25°, 20°, etc., or more than 30°, such as 35°, 40°, etc. Currently, the preferred range is ±15°. A set of image data can be taken at selected angular positions, such as every degree, or every fraction of a degree, or every several degrees of angle. The angular increments between the different positions for sets of image data need not be the same. For example, the increments around 0° can be less than those at the extremes of the angular positions, or vice versa. Currently, the preferred angular increment is 3°. The sets of image data can be taken after an incremental motion from one angular position of source 100 to another, and from one translational position of receptor 110 to another, such that source 100 and receptor 110 are stationary while a set of image data is being taken. Alternatively, one or both of source 100 and receptor 110 can move continuously while sets of image data are being taken, one set for each increment of continuous motion. In the currently preferred embodiment, in the example of continuous motion while taking image data both source 100 and receptor 110 move while image data are being taken.

FIG. 2 also illustrates schematically an electrical/electronic system 208 that interacts with the components discussed above. System 208 includes a control 210 for selectively energizing and otherwise controlling x-ray source 100, an arm rotation control 212 for selectively rotating C-arm 200 and support 204, a breast compression control 214 for selectively moving compression paddle 104 toward and away from breast platform 106, data readout electronics 216 coupled with x-ray receptor 110 to read out the sets of image data at the respective positions of source 100 and receptor 110 relative to immobilized breast 102, and an image reconstruction and display unit 218 coupled with data readout electronics 216 to receive the sets of image data from electronics 216 and to process the image data for reconstruction and other purposes and display images.

For a given position of breast 102, such as a position that is the same or similar to the CC position for a conventional mammogram, source 100 and receptor 110 can be positioned relative to immobilized breast 102 such that at the 0° position a center ray of the x-ray beam from source 100 would be substantially normal to receptor breast platform 106 and receptor 110. For a first set of image data, source 100 is at + (or −) 15° in a preferred example, and is gradually moved, continuously or intermittently to − (or +) 15°, with a set of image data taken every 3°. The angular range and the increment over which data sets are taken can each be selectively set by the operator, depending of characteristics of the breast being imaged and the screening and diagnostic needs, and can be different for different patients or from one to the other breast of the same patient. For example the source can move through angles that range from a fraction to a degree to several degrees from one imaging position to the next. Each set of image data is supplied by image readout 216 for processing at image reconstruction and display unit 218. Each set of image data can be taken at the same x-ray dose to the breast, and the dose at any one of the different imaging positions can be substantially less than that for a conventional mammogram. The x-ray dose can be substantially the same for each imaging position, but preferably the dose at one of the position, e.g., at or close to the 0° position, is the same or similar to dose for a conventional mammogram while the dose at the each of the other positions is less, preferably much less. Alternatively, the scan can begin with or end with an exposure close to the 0° position at a dose similar to a conventional mammogram, and the rest of the set of image data can be over the angular range with each exposure at an x-ray dose that is substantially less than that for a conventional mammogram. Thus, two types of images can be produced in accordance with the currently preferred embodiment while breast 102 is immobilized in the same position. One type is the same or is at least similar to a conventional mammogram, which can be read and interpreted in the manner familiar to health professionals. The other type is tomosynthetic images reconstructed from the image data and displayed either separately or as an adjunct to the display of the image that is the same or similar to a conventional mammogram. The process described above for one position of breast 102 can be repeated for another position. For example one process can be for a breast position in a manner that is the same or similar to positioning the breast for a conventional CC view, the breast can then be released, the support 204 and C-arm 200 rotated to other angular positions and the breast repositioned in a manner that is the same and similar to the position for an MLO view, and the procedure repeated.

Figure 3:
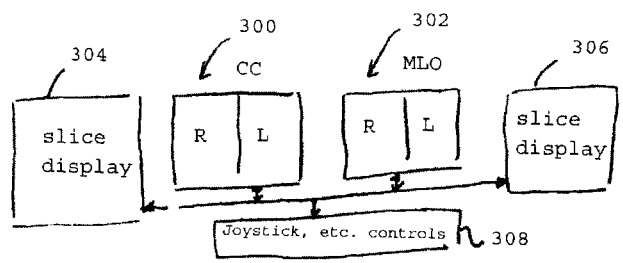
FIG. 3 illustrates a display arrangement showing both images that are the same or similar to conventional mammograms and tomosynthetic images according to a preferred embodiment.

FIG. 3 illustrates schematically a display according to a preferred embodiment, where 300 is a display that is the same or similar to a display for a conventional CC mammogram of two breasts and 302 is a similar display for a conventional MLO view. Another display 304 is close to display 300 and can display any one or more of several types of tomosynthetic images reconstructed from the image data taken at the different imaging positions. For example, if display 300 shows views of a right breast taken at or close to the 0° position in one imaging sequence of a total rotation of source 100 over the ±15° range, display 304 can show, at the option of the user, any one or more of the following views of the right breast: (1) one or more of the projection views taken at the different imaging positions; (2) one or more of several tomosynthetic views of thick slices of the right breast simulating projection views of the right breast taken at the same or similar angle as the view at display 300, with the slices having effective thicknesses selected by the user, such as from several mm to something less than the thickness of the immobilized breast, typically from several mm to about 1 cm; (3) one or more tomosynthetic views of thin slices of the right breast, each simulating a slice through the breast in a respective plane parallel to that of the view at display 300, where each thin slice has an effective thickness of about a mm or less; (4) thin and/or thick slices corresponding to planes that are not parallel to that of the view at display 300; (5) a scrolling image through any of the slices discussed above; and (6) a selected combination of the above displays. A similar display 306 can be associated with display 302, and show a similar selected views related to the images at display 302. FIG. 3 illustrates only one example according to preferred embodiments. Other arrangements also are contemplated, such as different windows on the same display for the different images, differently positioned displays, etc. The user can select the type of images for display, the thickness of a thick slice or a thin slice, the orientation of the slices for display, which slices to display where and in what order, whether to display thick or thin slices as static slides or to scroll through slice images as in a movie, etc. Controls 306 can be coupled to each of the displays, and can include manual inputs such as a joystick and/or other known interface devices and a suitably programmed computer to allow a user to control the images that are displayed. For example, the controls can include: (1) selecting one or more areas or volumes of interest at one or more of the displayed images and further processing the image data to form and display additional images of the area or volume of interest (for example, if a lesion is identified that is between tomosynthetic thin slices 32 and 37, the user can manually designate the corresponding area or volume and command the display of the thin slices in that area or volume, and other parameters such as the orientation of the thin slices); (2) identifying the position of an area or region of interest for use in additional procedures such as needle biopsy (for example, the user can designate with a cursor or in some other way a point in or an outline of a suspected lesion in the breast, and the xyz coordinates of the designated point, area, or volume); (3) the user can manually designate the desired thickness, arrangement, and other parameters of slices whose images are to be displayed, to thereby display images of slices that have user-selected thicknesses and other parameters, such as orientation, so that images of slices of different thicknesses and/or orientations can be displayed concurrently; and (4) the user can point to an area of interest in one of the displayed images and the system can automatically display one or more markers at corresponding or at least related locations in one or more of the other images that are being concurrently displayed.

At each imaging position, receptor 100 generates respective digital values for the pixels in a two-dimensional array. In one example, receptor 110 has a rectangular array of approximately 4096 by 3328 pixels, with a pixel size of approximately 70 micrometers in each of the column and row directions. The image data of a set (for a respective imaging position) can be processed either at the full spatial resolution of receptor 110, or at a lower effective spatial resolution, e.g., by binning several original pixel value's into a single, combined pixel value. For example, each set of 2×2 adjacent pixels can be combined into a single respective pixel value, thus achieving an effective spatial resolution of 140 micrometers in each direction. The binning can be in some other combination of original pixels, such as 2×3, and can be done by data readout electronics 216 or image reconstruction and display unit 218 (FIG. 2).

Figure 4:
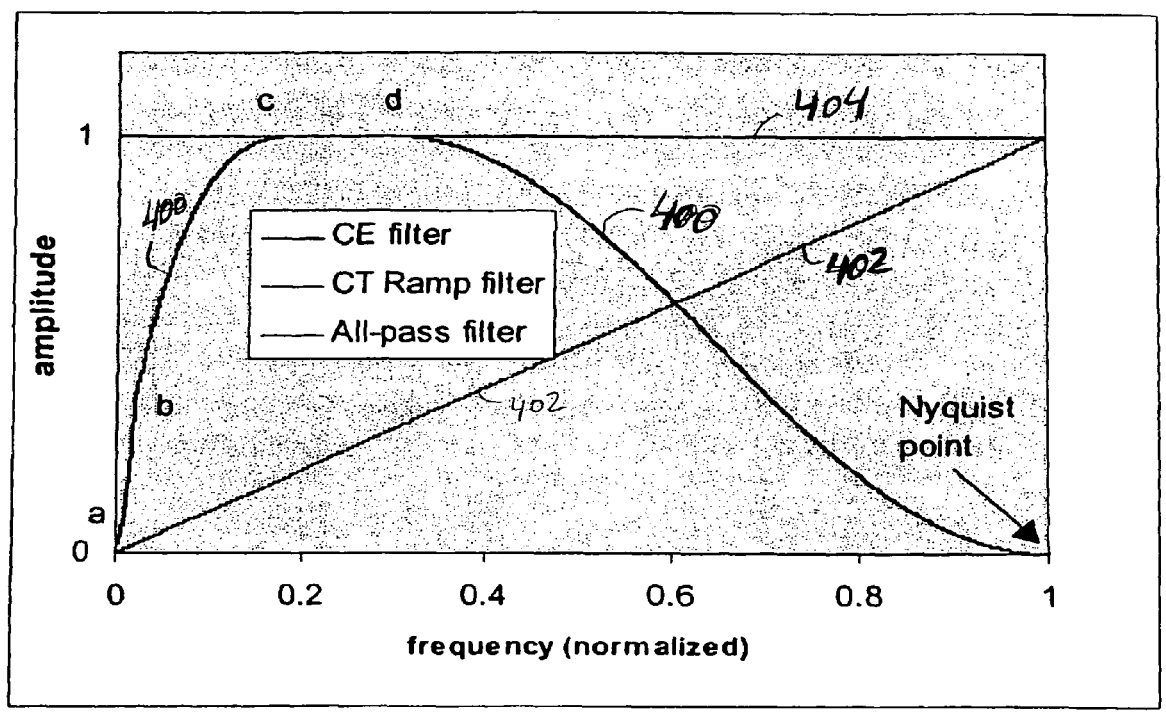
FIG. 4 illustrates in graph form a backprojection filter in the frequency domain used in a preferred embodiment, compared with a conventional ramp filter used in CT technology and an all-pass filter.

Image reconstruction is done using backprojection in the spatial domain or in the frequency domain as in CT technology but with a novel filter that differs from the ramp filter (in the frequency domain) used in CT reconstruction. See, e.g., G. Lauritsch, et al., *A theoretical framework for filtered backprojection in tomosynthesis*, SPIE Medical Imaging Conference, Vol. 3338, 1998, and U.S. Pat. No. 6,442,288, both incorporated here by reference. Referring to FIG. 4, the novel filter is represented by graph 400, while a graph 402 represents a conventional CT ramp filter, and a graph 404 represents an all-pass filter. As seen in FIG. 4, the novel filter according to a preferred embodiment rises sharply in amplitude at lower frequencies, between points a and c (in the range indicated at b), as compared with the conventional ramp filter, then levels off at intermediate frequencies to become the same as or close to an all-pass filter between points c and d, and then gradually drops off at higher frequencies. Using the novel filter produces significantly better breast images compared to using a conventional CT technology ramp filter.

Figure 5:
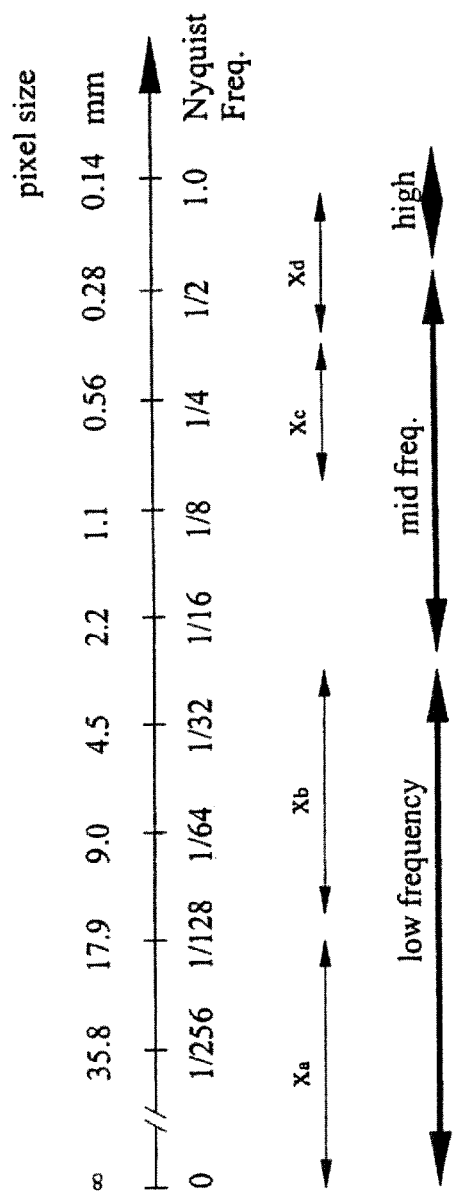
FIG. 5 illustrates coordinate values of a backprojection filter according to a preferred embodiment as control point values in the frequency domain in log scale.

FIG. 5 gives a sense of the values of the low, intermediate and high frequencies discussed in connection with FIG. 5. In FIG. 5, the frequency axis is plotted on log scale, and typically is related to spatial resolution of a few mm or more, i.e., it affects mainly to overall impression and flatness of the reconstructed image. With suitable suppression of low frequency content through frequency dependent weights defined by the shape of the novel filter, and gradual suppression of high frequency noise, a tomographic image with good image contrast at all frequency scales can be reconstructed and presented in accordance with a preferred embodiment. Preferably, the filtered backprojection reconstruction of tomographic images is carried out in the frequency domain, using well known processes with the novel filter. However, comparable filtered backprojection can be carried out in the spatial domain, as in known in CT technology, using direct convolution of image data with the spatial domain representation of the filter represented in the frequency domain in FIGS. 4 and 5. In either the frequency domain or in the spatial domain the novel filter can be applier to the image data to generate filtered data for backprojection, or backprojection can be carried out first, followed by a filtering operation. The reconstruction process preferably uses the direct fan-beam backprojection method known in CT technology, but with the novel filter, although it may be possible to use the image data to simulate sets of parallel beam paths for backprojection. The reconstructed thin slice images form a three-dimensional image of the breast, comprising voxel values for respective incremental volumes. These voxel values can then be combined as known in CT technology to synthesize any selected thin slice or thick slice in any selected orientation, and in any selected projection plane.

In a preferred embodiment, while each of all or most of the imaging positions uses lower x-ray dose than that of a conventional mammogram, higher KV can be used as compared with a conventional mammogram in order to boost signal levels from receptor 110 and improve signal-to-noise (SNR) ratios. In addition, preferable an x-ray tube with a Tungsten target is used to further exploit the advantage of higher kVp imaging of the breast, such as between 25 and 50 kVp with different x-ray beam filtration. A small focal spot, of the order of 1 mm or less, is preferred, although a larger focal spot of several mm can be used.

In other preferred embodiments, contrast enhanced breast tomosynthesis can be carried out, by obtaining tomosynthetic images as described above before injecting a contrast agent such as Iodine into the patient, then repeating the process after injection, and subtracting images of the pre-injection and post-injection sets. Another preferred embodiment involves time subtraction tomosynthesis, related to subtracting comparable images obtained at different times. Yet another is dual-energy breast tomosynthesis, whereby two tomosynthetic images at low and high energies are acquired and then subtracted, the two images being acquired through a process such as using successive scans at two different x-ray energy ranges or by alternating x-ray pulses of low and high energy to create the two images. Another other preferred embodiment involves obtaining and displaying both x-ray tomosynthetic images of a breast and ultrasound images of the same breast. Computer aided diagnosis, as known to those skilled in the art and as commercially used currently in the United States, can be applied to selected tomosynthetic images generated as described above.

Figure 6:
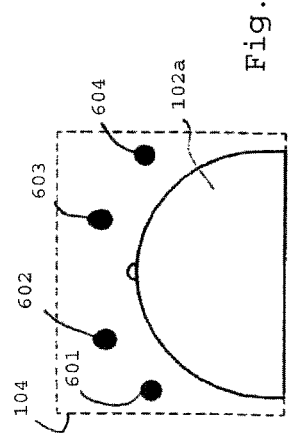
FIG. 6 illustrates the use of fiducial markers.

Fiducial markers are used in preferred embodiments for off-line (without a breast) mechanical positioning and calibration and/or on-line (while imaging a breast with x-rays) image based positioning encoding of moving components. The fiducial markers can be made of a material such as lead or another metal, and can be in the form of points or lines or arrows or crosses, at locations that would be imaged by the x-ray beam at receptor 110 simultaneously with the imaging of a breast 102 but outside the area of the breast image. The fiducial markers are integrated with compression paddle 104, or they can be at or near breast platform 106, or they can be supported separately from paddle 104, for example on a separate member that can be selectively brought into the path of the imaging x-ray beam or taken out of that path, e.g., to take an image that is the same or similar to a conventional mammogram. Different patterns or types of fiducial markers can be provided, for selection by the user. FIG. 6 illustrates an example of arranging fiducial markers 601, 602, 603 and 604 relative to an image of breast 102a on receptor 110, as seen in a top plan view when receptor 110 is horizontal and the fiducial markers are integrated in compression paddle 104.

An alternative embodiment, illustrated schematically in a front view in FIG. 7 and in side view in FIG. 8, is similar to the embodiment illustrated in FIGS. 1 and 2 except that receptor 110 is affixed to the end 200b of C-arm 200 that is opposite x-ray source 100. In this embodiment, receptor 110 moves relative to immobilized breast 102 along an arcuate path from one imaging position to another. Because the change in angle between receptor 110 and breast platform is small, it can be disregarded in processing the sets of x-ray image data. Alternatively, a geometric correction known to those skilled in the art can be applied to each set of image data to convert it to interpolated pixel values that would correspond to those that would have been obtained if receptor 110 had been parallel to and at the same distance from platform 106 at all imaging positions. The so corrected sets of image data can then be used in filtered back projections as described above.

In each of the embodiments of FIGS. 1-2 and FIGS. 7-8, antiscatter grid 108 may be selectively retractable, so that the user may take any selected set of x-ray image data with or without using grid 108. As in known in the art, grid 108 can be made to move relative to the x-ray beam during the taking of a set of image data. Similarly, the distance between breast platform 106 and receptor 110 can be selectively changed to effect magnification of the breast image recorded at receptor 110.

The invention claimed is:

1. A combo x-ray system for acquiring 2D and 3D images of the breast in a single compression, comprising:
an x-ray source, a flat panel digital x-ray imager, and a breast support and a compression paddle between the source and the imager, said compression paddle configured for selectively compressing the breast against the breast support;
a motion control configured for the source relative to a patient's breast while the breast remains immobilized in compression between the breast support and the compression paddle, and selectively energizing the source to emit x-rays through the breast to the imager at selected angular positions of the source relative to the breast;
a processor configured to control the imager to derive therefrom projection images of the compressed breast when the source is energized at each of said positions, wherein (i) at least one of the projection images is a mammogram image taken at a same or similar x-ray dose to the breast as a conventional mammogram and (ii) each of a multiplicity of the other projection images is a tomosynthesis projection image taken at an x-ray dose to the breast that is substantially less than that for a conventional mammogram;
said processor being further configured to process the multiplicity of the tomosynthesis projection images into tomosynthesis slice images representing slices of the patient's breast conforming to planes that are selectively the same or different from that of the mammogram image; and
a display configured for displaying said mammogram image and one or more of said tomosynthesis slice images selectively side by side or superimposed.

2. The system as in claim 1 in which the display is configured to display the mammogram image and the one or more tomosynthesis slice images on the same screen.

3. The system as in claim 1 including an anti-scatter grid and a grid support configured for selectively placing the grid in the path of x-rays from the breast to the imager and out of said path.

4. The system as in claim 1 in which a grid support is configured to place an anti-scatter grid in the path of x-rays from the breast to the imager while the imager is providing image data for the mammogram image but out of said path when the imager is providing image data for at least some of the tomosynthesis projection images.

5. A system for acquiring and displaying 2D and 3D breast x-ray images in combination, comprising:
a breast support and an x-ray source at one side of the breast support and a flat panel x-ray imager at a different side of the breast support;
a control configured for moving the source relative to a compressed patient's breast on the breast platform and selectively energizing the source to emit x-rays through the breast to the imager in the course of the source movement and selectively causing the imager to output image data for positions at which the source is energized, thereby causing the imager to acquire 2D mammogram image data and tomosynthesis projection image data;
wherein the tomosynthesis projection image data for a each of a multiplicity of said positions is taken at an x-ray dose to the breast that is substantially less than that for a conventional mammogram;
a processor configured to process the imager output and thereby form one or more 2D mammogram images and one or more 3D tomosynthesis slice images for slices of the compressed breast conforming to selected planes through the breast; and a display configured to display in combination and concurrently both one or more of said mammogram images and one or more of said 3D tomosynthesis slice images.

6. A system for taking x-ray mammogram images and tomosynthesis projection images of a patient's breast using the same equipment, comprising:
- an x-ray source, a flat panel x-ray imager and a breast support positioned between the source and the imager;
- a source support configured for selectively moving the source relative to the breast support;
- a control configured for selectively energizing the source in a mammogram position thereof relative to the breast support and causing the imager to provide image data for a mammogram image of a breast on the breast support, and selectively energizing the source at tomosynthesis positions thereof relative to the breast support and causing the imager to provide tomosynthesis image data for tomosynthesis projection images of a breast on the breast support;
- wherein the tomosynthesis image data for each of a multiplicity of said positions is taken at an x-ray dose to the breast that is substantially less than that for a conventional mammogram;
- a processor configured to process the mammogram image data to form one or more screening mammogram images and further configured to process the tomosynthesis image data to form one or more diagnostic tomosynthesis images; and
- a display configured for selectively displaying one or more of said screening mammogram images and a plurality of said tomosynthesis images.

7. The system as in claim 6 in which the display displays both at least one of the mammogram images and at least several of the tomosynthesis images concurrently.

8. The system as in claim 6 in which the image data for the mammogram and tomosynthesis positions is acquired during a single compression of a patient's breast.

9. A single combo system for selectively taking a mammogram image or tomosynthesis images of a patient's breast, comprising:
- an x-ray source, a flat panel x-ray imager and a breast support positioned between the source and the imager;
- a source support configured for selectively moving the source relative to the breast;
- a control configured for selectively energizing the source (i) in at least one mammogram position thereof relative to the breast support and causing the imager to provide mammogram image data for at least one mammogram image of a patient's breast on the breast support, and (ii) at tomosynthesis positions thereof relative to the breast support and causing the imager to provide tomosynthesis projection image data for tomosynthesis images of a breast on the breast support;
- wherein the tomosynthesis projection image data for each of a multiplicity of said tomosynthesis images is taken at an x-ray dose to the breast that is substantially less than that for a conventional mammogram;
- a processor configured to selectively process the mammogram image data to form at least one mammogram image and the tomosynthesis projection image data to form one or more tomosynthesis images; and
- a display configured for selectively displaying said mammogram image and one or more of said tomosynthesis images or previously taken mammogram or tomosynthesis images.

10. The system as in claim 9 in which the display is configured to display both at least one of the mammogram images and at least several of the tomosynthesis images concurrently.

11. The system as in claim 9 in which the image data for the mammogram and tomosynthesis positions is acquired during a single compression of a patient's breast.

12. A method of taking a mammogram image and/or tomosynthesis images using the same equipment and selectively displaying the mammogram and/or tomosynthesis images on the same display, comprising;
- providing an x-ray source that selectively moves relative to a patient's breast while the breast remains compressed, and a flat panel x-ray imager receiving x-rays from the source through the breast when the source is energized;
- selectively placing the source in at least one mammogram position relative to the breast and in plural tomosynthesis positions relative to the breast, and selectively energizing the source in said positions and extracting image data from the imager in response to x-rays from the source impinging thereon after passing through the breast;
- processing the image data extracted from the imager to form at least one mammogram image and plural tomosynthesis images;
- wherein the x-ray dose to the breast at each of a multiplicity of the tomosynthesis positions is substantially less than that for a conventional mammogram; and
- selectively displaying the image or images formed by the processor.

13. The method as in claim 12 in which the displaying comprises displaying both mammogram and tomosynthesis images side-by-side or superimposed.

14. The method as in claim 12 in which the displaying comprises displaying at the same time and side-by-side or superimposed both tomosynthesis images acquired with said equipment and at least one previously acquired mammogram image.

* * * * *

UNITED STATES PATENT AND TRADEMARK OFFICE
CERTIFICATE OF CORRECTION

PATENT NO. : 8,452,379 B2
APPLICATION NO. : 12/879807
DATED : May 28, 2013
INVENTOR(S) : Kenneth F. DeFreitas et al.

It is certified that error appears in the above-identified patent and that said Letters Patent is hereby corrected as shown below:

In the Claims

Claim 1, Column 10, Line 6, delete "configured for the source" and replace with --configured for moving the source--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*

Disclaimer

8,452,379 B2 - Kenneth F. DeFreitas, Patterson, NY (US); Baorui Ren, Andover, MA (US); Chris Ruth, Danvers, MA (US); Ian Shaw, Yorktown Heights, NY (US); Andrew P. Smith, Lexington, MA (US); Jay A. Stein, Boston, MA (US). X-RAY MAMMOGRAPHY WITH TOMOSYNTHESIS. Patent dated May 28, 2013. Disclaimer filed December 19, 2018, by the assignee, Hologic, Inc.

I hereby disclaim the following complete claims 6 and 9 of said patent.

*(Official Gazette, October 25, 2022)*